United States Patent [19]

Hsu et al.

[11] Patent Number: 5,346,913

[45] Date of Patent: Sep. 13, 1994

[54] N-IODOPROPARGYL HYDANTOIN COMPOUNDS, COMPOSITIONS, PREPARATION, AND USE AS ANTIMICROBIAL AGENTS

[75] Inventors: Adam C. T. Hsu, Lansdale; Steven H. Shaber, Horsham; Enrique L. Michelotti, Fort Washington, all of Pa.

[73] Assignee: Rohm and Haas Company, Philadelphia, Pa.

[21] Appl. No.: 888,572

[22] Filed: May 26, 1992

[51] Int. Cl.$^5$ .................. C07D 233/32; A61K 31/53
[52] U.S. Cl. .................. 514/389; 548/301.4; 548/317.1; 548/320.1; 548/320.5; 548/321.1
[58] Field of Search .................. 548/307, 301.4, 320.1, 548/320.5, 321.1, 317.1; 504/278; 514/389

[56] References Cited

U.S. PATENT DOCUMENTS

| | | | |
|---|---|---|---|
| 4,520,023 | 5/1985 | Schmitt et al. | 514/241 |
| 4,616,004 | 10/1986 | Edwards | 514/63 |
| 4,639,460 | 1/1987 | Rose et al. | 514/369 |
| 4,753,957 | 6/1988 | Chan et al. | 514/391 |

FOREIGN PATENT DOCUMENTS

| | | |
|---|---|---|
| 69855A2 | 1/1983 | European Pat. Off. . |
| 285270A1 | 10/1988 | European Pat. Off. . |
| 404498A3 | 12/1990 | European Pat. Off. . |

OTHER PUBLICATIONS

Chemical Abstracts, vol. 97, No. 13, Sep. 27, 1992, abstract No. 110009v, Substituted phenylhydantoin derivatives.

Journal of Medicinal Chemistry, vol. 35, No. 17, Aug. 21, 1992, pp. 3270-3279.

*Primary Examiner*—Johann Richter
*Assistant Examiner*—Catherine Scalzo
*Attorney, Agent, or Firm*—Michael B. Fein

[57] ABSTRACT

N-Iodopropargyl hydantoin compounds, methods of preparing, compositions comprising, and methods of use as antimicrobials and antifungal agents in a variety of applications.

6 Claims, No Drawings

N-IODOPROPARGYL HYDANTOIN COMPOUNDS, COMPOSITIONS, PREPARATION, AND USE AS ANTIMICROBIAL AGENTS

BACKGROUND OF THE INVENTION

1. Field of the Invention

This invention relates to control of microorganisms with chemical compounds.

2. Description of the Prior Art

Certain classes of iodopropargyl compounds have been proposed as microbicides but no compound within those classes has achieved commercial success.

U.S. Pat. No. 4,616,004 to Edwards discloses fungicidal activity for compounds of the formula

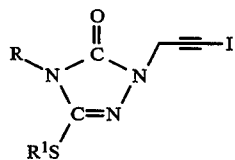

U.S. Pat. No. 4,639,460 to Rose shows compounds of the formula

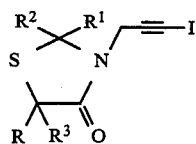

as fungicides.

U.S. Pat. No. 4,520,023 to Schmitt shows 3-(3-iodopropargyl)-benzo-1,2,3-triazolin-4-ones and their use as microbicidal agents.

U.S. Pat. No. 4,753,957 discloses certain intermediates made to prepare certain of the compounds of the invention of structure (III) which are known in the literature, although only when A=phenyl.

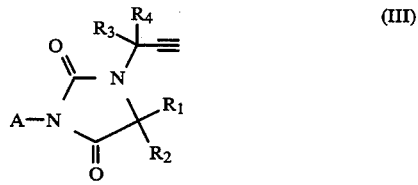

There was no suggestion in the prior art that compounds within the formula of the present invention would have utility in controlling microorganisms.

Some hydantoins are antimicrobially active. For example, 1,3-dihydroxymethyl-5,5-dimethylhydantoin (structure i) has long been used as an industrial microbicide; however, it has been known that this compound may release formaldehyde which is believed to be harmful to animals and humans.

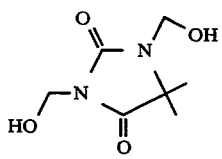

On the contrary, compounds of structure (I) and (II) in this invention do not release formaldehyde and therefore are safer to animals and humans.

SUMMARY OF THE INVENTION

It is an object of the present invention to provide new compounds for controlling microorganisms.

It is a further object to provide antimicrobial compounds which are safer in that they do not release formaldehyde.

A still further object is to provide methods of making such compounds, methods of using them, compositions comprising such compounds, and uses of such compositions.

These objects, and others which will become apparent from the following disclosure, are achieved by the present invention which comprises in one aspect compounds of the formulas (I) and (II) possessing antimicrobial activity,

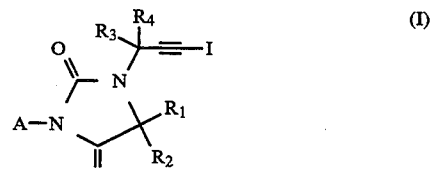

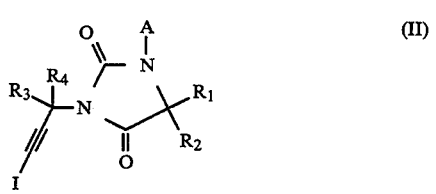

wherein A is selected from $C_1$ to $C_{12}$ straight or branched alkyl; benzyl; phenyl optionally substituted with halogen, nitro, cyano, haloalkyl ($C_1$-$C_3$), or alkoxy ($C_1$-$C_3$); allyl; alkynyl ($C_3$-$C_6$) optionally substituted with halogen; and hydrogen;

$R_1$, $R_2$ are independently selected from hydrogen; $C_1$-$C_3$ alkyl; and phenyl optionally substituted with halogen, nitro, alkoxy ($C_1$-$C_3$), or haloalkyl ($C_1$-$C_3$); or can be joined together along with the hydantoin ring carbon to which they are attached to form a saturated ($C_3$-$C_7$) or unsaturated ($C_5$-$C_7$) spirocycle; and $R_3$, $R_4$ are independently a hydrogen or a $C_1$-$C_3$ lower alkyl.

In another aspect the invention comprises a method of preparing such compounds comprising reacting compounds of the formulas (III) and (VIII)

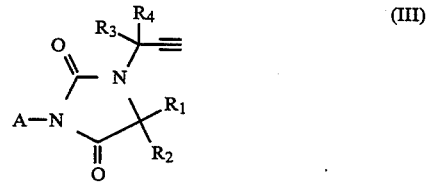

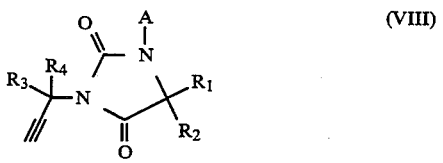

with an iodinating agent.

A further aspect comprises using a composition comprising the compound(s), or the compound(s) itself, as biocides to protect a materials such as wood, paint, adhesive, glue, paper, textile, leather, plastics, cardboard, lubricants, cosmetics, food, caulking, feed and industrial cooling water from attack by microorganisms.

A still further aspect comprises using the compounds and compositions comprising the compounds to control agricultural fungi.

DETAILED DESCRIPTION OF THE INVENTION AND THE PREFERRED EMBODIMENTS

The compounds of the invention are of formulas I and II as set forth above.

Preferred are compounds in which A is $C_1$-$C_{12}$ straight or branched alkyl; benzyl; phenyl optionally substituted with chlorine or riourine; $C_3$-$C_6$ alkynyl which is optionally substituted with halogen; or a hydrogen. Said halogen is most preferably iodine.

It is also preferred that $R_1$ and $R_2$ are independently selected from hydrogen; or $C_1$-$C_3$ alkyl. When $R_1$ and $R_2$ form a spirocycle, the compounds are not as active against certain organisms, and so such compounds are less preferred.

$R_3$, $R_4$ are preferably each hydrogen.

Specific embodiments of the compounds of the invention are the following:
1. 1-(3-iodo-2-propynyl)-3-(3,5-dichlorophenyl)-5-methylhydantoin
2. 1-(3-iodo-2-propynyl)-3-(4-chlorophenyl)-5-methylhydantoin
3. 1-(3-iodo-2-propynyl)-3-(4-fiuorophenyl)-5-methylhydantoin
4. 1-(3-iodo-2-propynyl)-3-(3,5-dichlorophenyl)-5,5-spirocyclopentane-hydantoin
5. 1-(3-iodo-2-propynyl)-3-(3,5-dichlorophenyl)-5,5-spirocyclohexane-hydantoin
6. 1-(3-iodo-2-propynyl)-3-(3,5-dichlorophenyl)-5,5-dimethylhydantoin
7. 1-(3-iodo-2-propynyl)-3-(3,5-dichlorophenyl)hydantoin
8. 1-(3-iodo-2-propynyl)-3-benzyl-5,5-dimethylhydantoin
9. 1-(3-iodo-2-propynyl)-3-n-butyl-5,5-dimethylhydantoin
10. 1-(3-iodo-2-propynyl)-3-n-octyl-5,5-dimethylhydantoin
11. 1,3-bis-(3-iodo-2-propynyl)-5,5-dimethylhydantoin
12. 3-(3-iodo-2-propynyl)-5,5-dimethylhydantoin
13. 1-(1,1-dimethyl-3-iodo-2-propynyl)-3-(3,5-dichlorophenyl)hydantoin
14. 3-(3-iodo-2-propynyl)-1-benzyl-5,5-dimethylhydantoin
15. 3-(3-iodo-2-propynyl)-hydantoin Compounds of formula I of this invention can be prepared by a variety of methods. One suitable method is reacting compounds of the structure III with an iodinating agent according to the following reaction scheme:

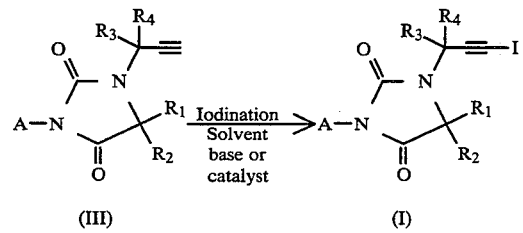

(III)      (I)

Suitable iodinating agents include, for example, iodine, an iodine-amino compound such as morpholine-iodine complex, and N-iodosuccinimide, the latter being the most preferred. When an iodine or iodo-amino compound is used, base should also be used, preferably sodium or potassium hydroxide, and solvent such as methanol, ethanol, and aqueous ethanol should also be used. When N-iodosuccinimide is used, a catalyst such as, for example, silver nitrate, or the like, should be used in presence of solvent such as acetone, methyl ethyl ketone, tetrahydrofuran, and the like. Reaction times of about 20 minutes to about 24 hours have been utilized successfully with reaction temperatures of about 0° C. to about 25° C.

The compounds of the intermediates of structure (III) can be prepared by a variety of methods. For example, the preparation of some of the intermediates of structure (III) are known in the literature (e.g. when A=phenyl in U.S. Pat. No. 4,753,957).

Alternatively, compounds of the structure (III) can also be prepared according to the following reaction scheme:

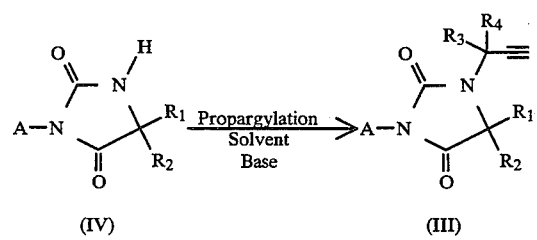

(IV)      (III)

The preparation of some of the starting materials of structure (IV) are known in the literature including methods cited in the U.S. Pat. No. 4,753,957, or can be prepared according to the following reaction scheme:

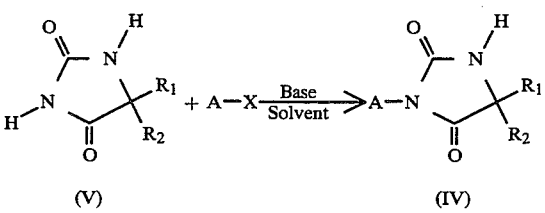

(V)      (IV)

X=$C_1$, Br, or I.

Suitable bases are, for example, potassium carbonate, potassium hydroxide, sodium hydroxide, and sodium carbonate.

Suitable solvents are, for example, acetone, methyl ethyl ketone, ethanol, methanol, and aqueous alcohol.

Compounds of the structure II of this invention can be prepared by a variety of methods including one depicted by the following reaction scheme (Equations a–c):

Equation a:

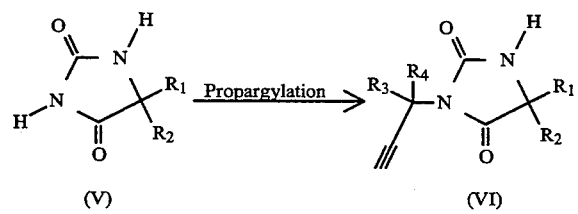

(V) → (VI)  Propargylation

Equation b:

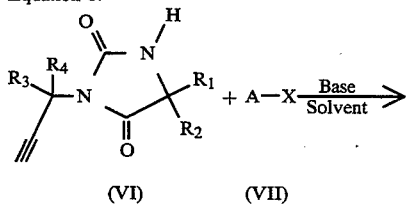

(VI) + A—X  Base/Solvent → (VIII)

(VII)

Equation c:

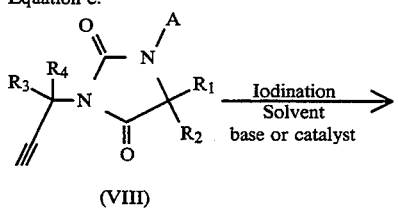

(VIII)  Iodination / Solvent / base or catalyst → (II)

When used as biocides, the compounds according to formula I or II are surprisingly effective bactericides, algaecides, and industrial fungicides, and are especially useful to protect cosmetic agents, cutting oils, soap or synthetic detergent, stabilizers, film forming materials, and other applications where biocides have been used in the past. The preferred biocidal utilities of the compositions are to protect wood, paint, adhesive, glue, paper, textile, leather, plastics, cardboard, lubricants, cosmetics, food, caulking, feed and industrial cooling water from microorganisms.

The amounts of the compound to be used in biocidal applications depend on the application. The useful amounts for a particular application are similar to amounts used for other microbicidal compounds.

The compound can be used in combination with other microbicides.

The Noiodopropargyl hydantoin compounds of this invention are useful as agricultural fungicides and as such can be applied to various loci such as the seed, the soil, or the foliage. These compounds as a class show broad spectrum antifungal activity when applied to crops such as vegetables, fruits, ornamentals, seed, turf, cereals, and vines among other plants. The compounds of this invention are especially strong against tomato light blight, wheat leaf rust, rice sheath blight, cucumber downey mildew, rice blast, and wheat powdery mildew. For such purposes, these compounds can be used in the technical or pure form as prepared, as solutions or as formulations. The compounds are usually taken up in a carrier or are formulated so as to render them suitable for subsequent dissemination as fungicides. For example, these chemical agents can be formulated as wettable powders, emulsifiable concentrates, dusts, granular formulations, suspension concentrates, aerosols, or flowable emulsion concentrates. In such formulations, the compounds are extended with a liquid or solid carrier and, when desired, suitable surfactants are incorporated.

It is usually desirable, particularly in the case of foliar spray formulations, to include adjuvants, such as wetting agents, spreading agents, dispersing agents, stickers, adhesives, and the like in accordance with agricultural practices. Such adjuvants commonly used in the art can be found in John W. McCutcheon, Inc. publication "Detergents and Emulsifiers, Annual."

In general, the compounds of this invention can be dissolved in certain solvents such as acetone, methanol, ethanol, DMF, pyridine, or DMSO and such solutions can be diluted with water. The concentrations of the solution can vary from about 1% to about 90% with a preferred range being from about 5% to about 50%.

For the preparation of emulsifiable concentrates, the compound can be dissolved in suitable organic solvents, or a mixture of solvents, together with an emulsifying agent which permits dispersion of the fungicide in water. The concentration of the active ingredient in emulsifiable concentrates is usually from about 10% to about 90%, and in flowable emulsion concentrates, can be as high as about 75%.

Wettable powders, suitable for spraying, can be prepared by admixing the compound with a finely divided solid, such as clays, inorganic silicates and carbonates, and silicas and incorporating wetting agents, sticking agents, and/or dispersing agents in such mixtures. The concentration of active ingredients in such formulations is usually in the range of from about 5% to about 98%, preferably from about 25% to about 75%. A typical wettable powder is made by blending 50 parts of a N-iodopropargyl hydantoin, 45 parts of a synthetic precipitated, hydrated silicon dioxide, sold under the trademark Hi-Sil®, 5 parts of sodium lignosulfate. In another preparation, a kaolin type (Barden) clay is used in place of the Hi-Sil in the above wettable powder, and in another such preparation, 25% of the Hi-Sil is replaced with a synthetic sodium silico aluminate, sold under the trademark Zeolex®7.

Dusts are prepared by mixing the N-iodopropargyl hydantoin compound with finely divided inert solids which can be organic or inorganic in nature. Materials useful for this purpose include botanical flours, silicas, carbonates, and clays. One convenient method of preparing a dust is to dilute a wettable powder with a finely divided carrier. Dust concentrates containing from about 20% to about 80% of the active ingredient are commonly made and are subsequently diluted to a range of about 1% to about 10% use concentration.

The N-iodopropargyl hydantoins can be applied as fungicidal sprays by methods commonly employed, such as conventional high gallonage, hydraulic sprays, aerial sprays, and dusts. The dilution rate of application will depend upon the type of equipment employed, the method of application, and diseases to be controlled, but the effective amount is usually from about 0.01 kg to about 20 kg of the active ingredient per hectare.

As a seed protectant, the amount of toxicant coated on the seed is usually at a dosage rate of from about 10 to about 250 grams and preferably from about 20 to about 60 grams per 50 kg of seed. As a soil fungicide, the chemical can be incorporated in the soil or applied to the surface usually at a rate of from about 0.5 to about 20 kg and preferably from about 1 to 5 kg per hectare. As a foliar fungicide, the toxicant is usually applied to growing plants at a rate of from about 0.1 to about 5 kg per hectare.

Fungicides which can be combined with the fungicides of this invention include:

(a) dithiocarbamate and derivatives, such as: ferbam, ziram, maneb, mancozeb, zineb, propineb, metham, thiram, the complex of zineb and polyethylene thiuram disulfide, dazomet, and mixtures of these with copper salts;

(b) nitrophenol derivatives, such as: dinocap, binapacryl, and 2-sec-butyl-4,6-dinitrophenyl isopropyl carbonate;

(c) heterocyclic structures, such as: captan, folpet, glyodine, anilazine, ditalimfos, 4-butyl-1,2,4-triazole, 5-amino-1-[bis(dimethylamino)phosphinyl]-3-phenyl-1,2,4-triazole, etradiazole, dithianon, thioquinox, benomyl, thiabendazole, 4-(2-chlorophenylhydrazono)-3-methyl-5-isoxazole, vinclozolin, iprodione, procymidone, triadimenol, triadimefon, bitertanol, prochloraz, fenarimol, bis-(p-chlorophenyl)-3-pyridinemethanol, bis-(p-chlorophenyl)-5-pyridinemethanol, triarimol, flutriafol, flusilazole, propiconazole, ectaconazole, myclobutanil, α-[2-(4-chlorophenyl)ethyl]-α-phenyl-1H-1,2,4-triazole-1-propanenitrile, hexaconazole, cyproconazole, tebuconazole, diniconazole, fluoroimide, pyridine-2-thiol-1-oxide, 8-hydroxyquinoline sulfate and metal salts thereof, 2,3-dihydro-5-carboxanilido-6-methyl-1,4-oxathiin-4,4-dioxide, 2,3-dihydro-5-carboxanilido-6-methyl-1,4-oxathiin, cis-N-[(1,1,2,2-tetrachloroethyl)thiol]-4-cyclohexene-1,2-dicarboximide, cycloheximide, dehydroacetic acid, captafol, ethirimol, quinomethionate, D,L-methyl-N-(2,6-dimethylphenyl)-N-(2-methoxyacetyl)alanine methyl ester, D,L-methyl-N-(2,6-dimethylphenyl)-N-chloroacetyl-D,L-2-aminobutyrolactone, D,L-N-(2,6-dimethylphenyl)-N(phenylacetyl)alanine methyl ester, 5-methyl-5-vinyl-3-(3,5-dichlorophenyl)-2,4-dioxo-1,3-oxazolidine, 3-(3,5-dichlorophenyl)-5-methyl-5-(methoxymethyl)-1,3-oxazolidi-2,4-dione, 3-(3,5-dichlorophenyl)-1-isopropylcarbamoylhydantoin, 2-cyano-N-(ethylaminocarbonyl)-2-methoximino]acetamide, fenpropimorph, fenpropidine, 2,6-dimethyl-N-tridecylmorpholine, dodemorph, and triforine;

(d) miscellaneous halogenated fungicides, such as: chloranil, dichlone, chloroneb, tricamba, TCPN, dichloran, 2-chloro-1-nitropropane, polychloronitrobenzenes such as pentachloronitrobenzene (PCNB), and tetrafluorodichloroacetone;

(e) fungicidal antibiotics, such as: griseofulvin, kasugamycin, polyoxin, validamycin, and streptomycin;

(f) copper-based fungicides, such as: copper hydroxide, cuprous oxide, basic cupric chloride, basic copper carbonate, copper terephthalate, copper naphthenate and Bordeaux mixture; and (g) fungicides, such as: dodine, phenylmercuric acetate, N-ethylmercuri-1,2,3,6-tetrahydro-3,6-en d omethano-3,4,5,6,7,7-hexachlorophthalimide, phenylmercuric monoethanol ammonium lactate, p-dimethylaminobenzene sodium sulfonate, methyl isothiocyanate, 1-thiocyano-2,4-dinitrobenzene, 1-phenylthiosemicarbazide, nickel-containing compounds, calcium cyanamide, lime sulfur, thiophanate-methyl, flutolanil, edinophos, isoprothiolane, propenazole, and tricyclazole.

The following examples are presented to illustrate a few embodiments of the invention. All parts and percentages are by weight unless otherwise indicated.

EXAMPLES

EXAMPLE 1

Preparation of 1-(3-iodo-2-propynyl)-3-(3,5-dichlorophenyl)-5-methylhydantoin (Compound No. 1)

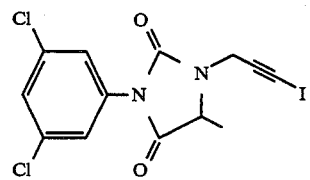

(a) Preparation of Methyl 2-propargylaminopropionate

Into a 250 mL round bottom flask were placed propargylamine (26 g, 0.47 mole), methyl-2-bromopropionate (78.8 g, 0.47 mole), and sodium bicarbonate (39.7 g, 0.47 mole). The reaction mixture was heated at 80° C. overnight. It was cooled and poured into water (200 mL). Extraction with ether provided 45 grams of crude product which was further purified by vacuum distillation (94°–95°/3 mm Hg) to give 25 grams of desired product.

(b) Preparation of 1-(2-propynyl)-3-(3,5-dichlorophenyl)-5-methylhydantoin

To a solution of methyl 2-propargylaminopropionate (10 g, 0.07 mole) in toluene (100 mL) with 2 drops of stannous octonoate was added 3,5-dichlorophenylisocyanate (14.5 g, 0,077 mole) in small portions. The resulting mixture was heated at 100° C. for 3 hours. It was then washed with water twice and dried over sodium sulfate. Solvent was evaporated to give a thick, yellow oil. Material was further purified by passing it through a silica gel column using 30/70 ethyl acetate/hexane as eluent to give 18 grams of a light yellow oil which solidified on standing. The solids were triturated in boiling hexane and collected by suction filtration; mp 105°–106° C., NMR and elemental analysis confirmed the desired structure.

(c) Preparation of 1-(3-iodo-2-propynyl)-3-(3,5-dichlorophenyl)-5-methylhydantoin. To a stirred solution of 1-(2-propynyl)-3-(3,5-dichlorophenyl)-5-methylhydantoin (2.97 g, 10 mmole) in dry acetone (30 mL) was added N-iodosuccinimide (5.2 g, 23 mmole), followed by silver nitrate (50 mg, 0.29 mmole) at room temperature. The resulting mixture was stirred at room temperature for 2 hours and diluted with water (200 mL). The resulting precipitate was collected by suction filtration, yielding 3.5 grams of expected compound as a light yellow solid, mp 122°–126° C. An NMR spectrum showed the desired compound.

EXAMPLE 2

Preparation of 3-(3-Iodo-2-propynyl)-5,5-dimethylhydantoin (Compound No. 12)

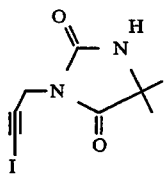

(a) Preparation of 3-(2-propynyl)-5,5-dimethylhydantoin

To a stirred solution of 5,5-dimethylhydantoin (10 g, 78 mmole) in methyl ethyl ketone (500 mL) at room temperature was added potassium carbonate (13 g, 94.1 mmole), followed by propargyl bromide (14 g, 80% in toluene, 94.1 mmole). The reaction mixture was then refluxed for 2.5 hr. The mixture was cooled to room temperature and the solid was filtered by suction filtration. The filtrate was concentrated on a rotary evaporator to give 12.5 g (96%) of 3-(2-propynyl)-5,5-dimethylhydantoin as a yellow solid, mp=156°–160° C. An NMR spectrum showed the desired product with a purity about 95%. This intermediate was subjected to the next step without further purification.

(b) Preparation of 3-(3-iodo-2-propynyl)-5,5-dimethylhydantoin

To a stirred solution of 3-(2-propynyl)-5,5-dimethylhydantoin (1 g, 60 mmole) in CCl4 (20 mL) at room temperature was added N-iodosuccinimide (1.6 g, 7.1 mmole). Dry acetone was added until all materials were dissolved. To the above clear solution was added silver nitrate (0.1 g, 0.58 mmole) and the reaction mixture was stirred at room temperature for 2 hr. The mixture was diluted with water (60 mL) and was extracted with ethyl acetate (3×50 mL). The organic layer was washed with saturated sodium chloride solution (75 mL) and dried with sodium sulfate. After filtering off drying agent and evaporating the solvents, a light yellow solid of 3-(3-iodo-2-propynyl)-5,5-dimethylhydantoin was obtained, 1.6 g (91%), mp=118°–126° C. An NMR spectrum also showed the desired product.

EXAMPLE 3

Preparation of 1,3-Bis-(3-iodo-2-propynyl)-5,5-dimethylhydantoin (Compound No. 11)

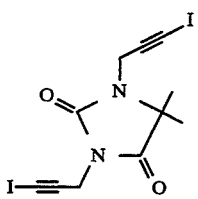

(a) Preparation of 1,3-Bis-(2-propynyl)-5,5-dimethylhydantoin

To a stirred solution of 3-(2-propynyl)-5,5-dimethylhydantoin (3 g, 18.1 mmole) in methyl ethyl ketone (125 mL) at room temperature was added K2CO3 (2.8 g, 20.3 mmole), followed by propargyl bromide (3 g, 80% in toluene, 20.2 mmole). The reaction mixture was then refluxed for 24 hr. The reaction mixture was cooled to room temperature and was diluted with water and extracted with methylene chloride (3×125 mL). The organic layer was washed with saturated NaCl and dried over MgSO4. Evaporation of the volatiles yielded 3.3 g (89 %) of 1,3-di-propargyl-5,5-dimethylhydantoin as a light yellow semi-solid. An NMR spectrum showed the desired structure. This intermediate was subjected to the next step without further purification.

(b) Preparation of 1,3-Bis-(3-iodo-2-propynyl)-5,5-dimethylhydantoin

To a stirred solution of 1,3-bis-(2-propynyl)-5,5-dimethylhydantoin (1.1 g, 5.4 mmole) in dry acetone (30 mL) at room temperature was added N-iodosuccinimide (2.8 g, 12.4 mmole), followed by silver nitrate (50 mg, 0.29 mmole). The reaction mixture was stirred at room temperature for 2 hr. The mixture was then diluted with water (200 mL) and an oily material was obtained by suction-filtration. The oil was dissolved in methylene chloride (50 mL) and dried over MgSO4. After evaporation, a viscous, oily product was obtained yielding 1.7 g (69 %). TLC (EtOAc/Hexane=1:1) showed one spot with Rf=0.51. An NMR spectrum also showed the desired product.

EXAMPLE 4

Preparation of 3-benzyl-1-(3-iodo-2-propynyl-5,5-dimethylhydantoin (Compound No. 8)

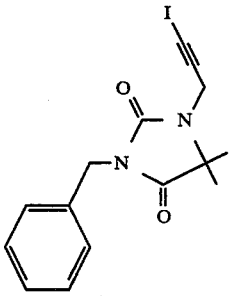

(a) Preparation of 3-benzyl-5,5-dimethylhydantoin

To the stirred solution of 5,5-dimethylhydantoin (7 g, 54.7 mmole) in dry acetone (150 mL) under nitrogen were added potassium carbonate (10.6 g, 76.8 mmole) and benzylbromide (11.2 g, 65.9 mmole) at room temperature. The reaction mixture was refluxed for 20 hr. The reaction mixture was cooled to room temperature and the solid was filtered off by suction filtration. The titrate was concentrated on a rotary evaporator to give a residue. The residue was diluted with ethyl acetate and washed with water and brine, dried over sodium sulfate and evaporated to give 10.9 g (yield=91.3 %) of 3-benzyl-5,5-dimethylhydantoin as a white solid, mp=101°–104° C. This intermediate was subjected to the next step without further purification.

(b) Preparation of 3-benzyl-1-propargyl-5,5-dimethylhydantoin

To a stirred solution of 3-benzyl-5,5-dimethylhydantoin (9.5 g, 43.6 mmole) in acetone (100 mL) at room temperature were added potassium carbonate (8.4 g, 60.9 mmole) and propargyl bromide (7.1 g of 80 % in toluene, 47.7 mmole). The reaction mixture was refluxed for 16 hr; cooled to room temperature and the solid was filtered off by suction-filtration. The filtrate was concentrated and the resultant residue was diluted with ethyl acetate and washed with water and brine. The organic layer was dried over sodium sulfate. After evaporation, a yellow crude oil was obtained. A pure product, 5.5 g (yield=50%) of 3-benzyl-1-propargyl-5,5-dimethylhydantoin as a yellow oil, was obtained by column chromatography on silica gel eluting with ethyl acetate:hexane (1:1 ).

(c) Preparation of 3-benzyl-1-(3-iodo-2-propynyl)-5,5-dimethylhydantoin

To a solution of 3-benzyl-1-propargyl-5,5-dimethylhydantoin (2 g, 7.81 mmole) in acetone (35 mL) at room temperature was added N-iodosuccinimide (2.1 g, 9.2 mmole), followed by silver nitrate (0.265 g, 1.56 mmole). The reaction mixture was stirred at room temperature for 5 hr. The reaction mixture was then passed through Celite by suction-filtration and washed with acetone. The filtrate was concentrated on a rotary evaporator and diluted with ethyl acetate. The solution was washed with water and brine and dried over sodium sulfate. The solvent was evaporated on a rotary evaporator to give 1.9 g of 3-benzyl-1-(3-iodo-2-propynyl)-5,5-dimethylhydantoin as a light brown oil which slowly solidified, mp=83°–85° C. An NMR spectrum also showed the desired structure.

EXAMPLE 5

Preparation of
1-benzyl-3-(3-iodo-2-propynyl)-5,5-dimethylhydantoin
(Compound No. 14)

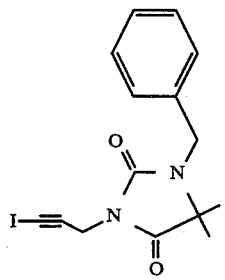

(a) Preparation of 3-(propyn-2-yl)-5,5-dimethylhydantoin

To a stirred solution of 5,5-dimethylhydantoin (19.2 g, 0.15 mole) in dry methyl ethyl ketone (500 mL) under nitrogen were added potassium carbonate (31.12 g, 0.225 mole) and propargyl bromide (20.88 g, 0.18 mole) at room temperature. The reaction mixture was refluxed for 24 hr. The reaction mixture was then cooled to room temperature and the solid was filtered off by suction filtration. The filtrate was concentrated on a rotary evaporator to give a residue. The residue was diluted with ethyl acetate, washed with water and brine, dried over sodium sulfate and evaporated to give 18.9 g (yield=76 %) of 3-(propyn-2-yl)-5,5-dimethylhydantoin as a white solid, mp=164°–165° C. This intermediate was subjected to the next step without further purification.

(b) Preparation of 1-benzyl-3-(propyn-2-yl)-5,5-dimethylhydantoin

To a stirred solution of 3-(propyn-2-yl)-5,5-dimethylhydantoin (4.0 g, 24 mmole) in methyl ethyl ketone (500 mL) at room temperature was added potassium carbonate (4.98 g, 36 mmole), followed by benzyl bromide (4.9 g of 80 % in toluene, 29 mmole). The reaction mixture was refluxed for 72 hr, cooled to room temperature and the solid was filtered off by suction filtration. The filtrate was concentrated and the resultant residue was diluted with ethyl acetate and washed with water and brine. The organic layer was dried over sodium sulfate. After evaporation, an amber oil was obtained. A pure product, 2.1 g (yield=34 %) of 1-benzyl-3-propargyl-5,5dimethylhydantoin was obtained as an oil from column chromatography on silica gel, eluting with ethyl acetate:hexane (1:1).

(c) Preparation of 1-benzyl-3-(3-iodo-2-propynyl)-5,5-dimethylhydantoin

To a stirred solution of 1-benzyl-3-propargyl-5,5-dimethylhydantoin (1.2 g, 4.6 mmole) in acetone (50 mL) at room temperature was added finely ground silver nitrate (0.15 g. 0.8 mmole), followed by N-iodosuccinimide (1.16 g, 5.2 mmole). The reaction mixture was stirred at room temperature for 5 hr. The reaction mixture was then passed through Celite by suction filtration and washed with acetone. The titrate was concentrated on a rotary evaporator and diluted with ethyl acetate. The solution was washed with water and brine and dried over sodium sulfate. The solvent was evaporated on a rotary evaporator to give 1.5 g of 1-benzyl-3-(3-iodo-2-propynyl)-5,5-dimethylhydantoin as a solid, mp=109°–112° C. An NMR spectrum also showed the desired structure.

EXAMPLE 6

Characterization of Compounds of Invention

Table (1) shows the structures and the physical data of these representative compounds.

TABLE (1)

Structures and Physical Data

| Compound | Structure | $R_1$ | $R_2$ | $R_3$ | $R_4$ | A | $^1$H-NMR Chemical Shift (ppm) or Melting Point |
|---|---|---|---|---|---|---|---|
| 1 | I | H | $CH_3$ | H | H | 3,5-$Cl_2$-ph | 122–126° C. |
| 2 | I | H | $CH_3$ | H | H | 4-Cl-ph | 94–100° C. |
| 3 | I | H | $CH_3$ | H | H | 4-F-ph | 107–109° C. |
| 4 | I | —$(CH_2)_4$— | | H | H | 3,5-$Cl_2$-ph | 7.50(2H, s) 7.38(1H, s) 4.48(2H, s, $CH_2$) 1.50–2.30(8H, m) |
| 5 | I | —$(CH_2)_5$— | | H | H | 3,5-$Cl_2$-ph | 120–124° C. |
| 6 | I | $CH_3$ | $CH_3$ | H | H | 3,5-$Cl_2$-ph | 140–144° C. |
| 7 | I | H | H | H | H | 3,5-$Cl_2$-ph | 140–146° C. |
| 8 | I | $CH_3$ | $CH_3$ | H | H | $CH_2$-ph | 83–85° C. |
| 9 | I | $CH_3$ | $CH_3$ | H | H | $(CH_2)_3CH_3$ | 4.32(2H, s, $CH_2$) 3.52(2H, t, $CH_2$) 1.60(2H, m, $CH_2$) 1.49(6H, s, 2$CH_3$) |

TABLE (1)-continued

Structures and Physical Data

| Compound | Structure | $R_1$ | $R_2$ | $R_3$ | $R_4$ | A | $^1$H-NMR Chemical Shift (ppm) or Melting Point |
|---|---|---|---|---|---|---|---|
| 10 | I | $CH_3$ | $CH_3$ | H | H | $(CH_2)_7CH_3$ | 1.35(2H, m, $CH_2$)<br>0.95(3H, t, $CH_3$)<br>4.34(2H, s, $CH_2$)<br>3.52(2H, t, $CH_2$)<br>1.50(6H, s, $2CH_3$)<br>1.80–1.10(12H, m, $6CH_2$)<br>0.90(3H, t, $CH_3$) |
| 11 | I | $CH_3$ | $CH_3$ | H | H | $CH_2\text{—}\equiv\text{—I}$ | 4.32(2H, s, $CH_3$) |
| 12 | II | $CH_3$ | $CH_3$ | H | H | H | 4.22(2H, s, $CH_2$)<br>1.44(6H, s, $2CH_3$)<br>118–126° C. |
| 13 | I | H | H | $CH_3$ | $CH_3$ | 3,5-$Cl_2$-ph | 116–124° C. |
| 14 | II | $CH_3$ | $CH_3$ | H | H | $CH_2$-ph | 109–112° C. |
| 15 | II | H | H | H | H | H | 149–151° C. |

EXAMPLE 7

Biological Activity versus non-iodo analogues

Comparative tests to demonstrate activity against industrial fungi and bacteria of several embodiments of the compounds of the invention were carried out. The compounds identified with a prime (') were the non-iodo analogues of the invention compounds, i.e., the compounds of formula III or IV. The results of MIC tests of compounds of this invention are shown in Table 2. All data are reported in ppm of active ingredient required to control the respective organism. The indication "No In." means that the compound had no inhibitory activity at 500 ppm which was the maximum tested, and so if the "No In." compound were active, the minimum inhibitory concentration would be above 500 ppm. The comparative tests were not run side-by-side, but were run on different days using the same methods. Comparing 13 and 13' appears to be the result of experimental error.

A minimum inhibitory concentration (MIC) value is obtained using a broth, two-fold serial dilution test performed as follows: A stock solution or dispersion of the test compound, typically at a concentration of 1%, is made in a 5:3:2 solvent solution of acetone, methanol, and water. A volume of the stock solution is dispensed into culture media to give an initial starting test concentration of the compound of 500 ppm or 250 ppm.

When the test is ready to be done, each vessel in the dilution series, except the first vessel, contains an equal volume of compound free broth. The first vessel contains twice the volume of broth with the starting concentration of test compound. One half of the broth from the first vessel is transferred to the second vessel. After being mixed, one half the resulting volume is removed from the second vessel and transferred to the third vessel. The entire cycle is repeated sufficiently to give a series of concentrations amounting to 500, 250, 125, 63, 31, 16, 8, and 4 ppm or 250, 125, 63, 32, 16, 8, 4, 2, 1, 0.5, 0.25, and 0.12, respectively.

Each vessel is then inoculated with a cell suspension of the appropriate test organism. Bacteria are grown in broth and fungi on agar slants and algae is grown in cooling tower media for a time and at a temperature appropriate to the species being tested. At the end of the growth period, the broth is vortexed to disperse the cells. In the case of fungi, the spores are harvested by pipetting water onto the slant and dislodging the spores with a sterile loop. The cell/spore suspension is standardized by controlling incubation time, temperature, and the volume of the diluent. The suspension is then used to inoculate the vessels containing the broth compound. The vessels are then incubated at the appropriate temperature. After the incubation, the vessels are examined for growth/no growth. The MIC is defined as the lowest concentration of compound that results in complete inhibition of growth of the test organism.

The organisms tested to demonstrate biocidal activity include:

BACTERIA: *Pseudomonas fluorescens* (Ps.fl), gram negative; *Pseudomonas aerugenosa* (Ps.ae), gram negative; *Escherichia coli* (E.c), gram negative; and *Staphylococcus aureus* (S.a), gram positive.

INDUSTRIAL FUNGI: *Aspergillus niger* (A.n); *Aureobasidium pullulans* (A.p)

TABLE 2

Comparative Activity Against Industrial Fungi and Bacteria (MIC, ppm)

| Compound # | Psae M9G | Psae TSB | Ecol M9G | Ecol TSB | Saur M9G | Saur TSB | Anig TSB |
|---|---|---|---|---|---|---|---|
| 1 | No In. | No In. | No In. | No In. | No In. | No In. | 0.5 |
| 1' | No In. | No In. | No In. | No In. | No In. | No In. | No In. |
| 2 | No In. | No In. | No In. | 500 | No In. | No In. | 2 |
| 2' | No In. | No In. | No In. | No In. | No In. | No In. | No In. |
| 3 | No In. | No In. | No In. | 250 | No In. | No In. | 4 |
| 3' | No In. | No In. | No In. | No In. | No In. | No In. | No In. |
| 4 | No In. | No In. | No In. | No In. | No In. | No In. | 16 |
| 4' | No In. | No In. | No In. | No In. | No In. | No In. | No In. |
| 5 | No In. | No In. | No In. | No In. | No In. | No In. | No In. |
| 5' | No In. | No In. | No In. | No In. | No In. | No In. | No In. |
| 6 | No In. | No In. | No In. | No In. | 8 | 2 | 1 |
| 6' | No In. | No In. | No In. | No In. | 8 | 8 | No In. |

TABLE 2-continued

Comparative Activity Against Industrial Fungi and Bacteria (MIC, ppm)

| Compound # | Psae M9G | Psae TSB | Ecol M9G | Ecol TSB | Saur M9G | Saur TSB | Anig TSB |
|---|---|---|---|---|---|---|---|
| 7 | No In. | No In. | No In. | No In. | 16 | 8 | 1 |
| 8 | 32 | 125 | 64 | 125 | 16 | 16 | <0.25 |
| 8' | No In. | No In. | No In. | No In. | No In. | No In. | No In. |
| 9 | 64 | 500 | 16 | 500 | 4 | 16 | 2 |
| 9' | No In. | No In. | No In. | No In. | No In. | No In. | No In. |
| 10 | 125 | No In. | 250 | No In. | 2 | 4 | 4 |
| 10' | No In. | No In. | 500 | No In. | 32 | 63 | No In. |
| 11 | 125 | — | 64 | — | 32 | — | <4 |
| 11' | No In. | No In. | No In. | No In. | No In. | No In. | No In. |
| 12 | 250 | No In. | 125 | 250 | 125 | 16 | 8 |
| 12' | No In. | No In. | No In. | No In. | No In. | No In. | No In. |
| 13 | No In. | No In. | No In. | No In. | No In. | No In. | 8 |
| 13' | No In. | No In. | No In. | No In. | 8 | 8 | No In. |
| 14 | No In. | No In. | 125 | 250 | No In. | 64 | 4 |
| 14' | No In. | No In. | No In. | No In. | No In. | No In. | No In. |
| 15 | 250 | 500 | 64 | 64 | 64 | 125 | 8 |
| 15' | No In. | No In. | No In. | No In. | No In. | No In. | 500 |

EXAMPLE 8

In-Vitro Plant Disease Tests of Compounds

The organisms employed in the test are:
PYU *Pythium ultimum* (Oomycete)
PHY *Phytophthora capsici* (Oomycete)
PIR *Piricularia oryzae* (Ascomycete)
HEL *Cochliobolus sativus* (Ascomycete)
BOC *Botrytis cinerea* (Ascomycete)
FUS *Fusarium roseum* (Ascomycete)
SEP *Septoria nodorum* (Ascomycete)
RHI *Rhizoctonia solani* (Basidiomycete)
XAN *Xanthomonas campestris* (bacterium)

Methods:

1. Culture maintenance

Transfers in steps 1 and 2 are done in a laminar flow hood. All 8 fungi and the bacterium used in this test are transferred and maintained on potato dextrose agar plates each week (2 plates/organism). Organisms are used when they are the following ages: a. 1 week old: PYU, PHY, RHI; b. 2 weeks old: XAN, PIR, BOC, HEL, FUS, SEP, COL, MON, CER, UST, ALT; c. 3 weeks old: PSH, VEN. *Pythium ultimum* and *Phytophthora capsici* are transferred to asparagine-sucrose broth shake cultures (ASB). *Rhizoctonia solani*, *Fusarium roseum*, and *Xanthomonas campestris* are maintained in yeast extractdextrose broth (YDB) on a shaker. Culture flasks are inoculated with 6 mycelial plugs each (except for Pythium which is inoculated with only 3 plugs) taken from PDA plates. All liquid shaker cultures are used after 2 days growth.

2. Inoculum preparation

Conidia and mycelium from PIR, BOC, HEL, SEP, COL, MON, CER, PSH, UST and ALT are lightly scraped off into YDB so that mostly conidia are used as inoculum. The conidial suspension is strained through a double layer of cheesecloth to remove mycelial clumps. One plate produces enough conidia or mycelium to inoculate 100 ml of YDB. XAN broth culture is poured (1 mL culture/100 ml broth) into YDB. PYU, PHY, RHI and FUS cultures are ground up (2–3 5 second bursts in a blender) and all but Pythium and Phytophthora are filtered through a double layer of sterile cheesecloth to remove large mycelial clumps. Ten ml of the culture solutions of *R. solani* and *F. roseum* are added to 90 ml of YSB and 10 ml of the *P. capsici* is added to 90 ml ASB. Two ml of the culture solution of *P. ultimum* is added to 98 ml of ASB. Care must be made not to overinoculate (e.g. solutions should appear fairly clear to the eye, yet when held up to light a faint cloudiness should be visible) or standards will not behave properly. The inoculum mixtures are placed in microtiter plates using a 12-tipped pipet. 175 μl (single dose) or 100 μl (dose-response test) of inoculum broth is placed in each well of the microtiter plates. The plates with inoculated media are placed in the refrigerator overnight. There are two replications per treatment.

3. Addition of compounds

This operation is carried out in a chemistry hood. Six microtiter plates have 245 microliters of sterile water added to their wells ahead of time. 10 Mg a.i. of the compounds are placed in 1 ml 1:1 acetone:methanol. 5 Microliters of this solution (6 microliters in the case of the 50 ppm dose) is pipetted into the microtiter plates containing the sterile water according to the grid. There are 45 compounds and 3 scattered control treatments per plate. There are 2 replicates per treatment. 25 Microliters of solution is transferred to the inoculated plates with a 96 well replicator. The replicator is flame sterilized with alcohol, rinsed with sterile water, and blotted on sterile paper towels between each transfer.

TABLE 3

The Results of In-Vitro Plant Disease Tests

| Compound | Dose (PPM) | % Control PYU | XAN | PIR | PHY | BOC | HEL | RHI | FUS | SEP |
|---|---|---|---|---|---|---|---|---|---|---|
| 11 | 50 | 100 | 0 | 100 | 100 | 95 | 100 | 100 | 100 | 100 |
| 11 | 25 | 100 | 0 | 100 | 0 | 0 | 90 | 100 | 0 | 100 |
| 12 | 25 | 100 | 0 | 90 | 100 | 0 | — | 100 | 75 | — |

EXAMPLE 9

Agricultural Fungicide Evaluations of Compounds

The compounds of this invention were tested for fungicidal activity in-vivo against cucumber downy mildew (CDM), rice blast (RB), rice sheath blight (RSB), tomato late blight (TLB), wheat powdery mildew (WPM), wheat stem rust (WSR) wheat leaf rust (WLR) and wheat leaf blotch (SNW). The results are shown in Tables 4–6. In tests on cereals (except for rice plants used for testing rice blast), the plants were trimmed about 24 hours prior to the application of the fungicide compound to provide a uniform plant height and to facilitate uniform application of the compound and inoculation with the fungus. The compounds were dissolved in a 2:1:1 mixture of water, acetone, and methanol, sprayed onto the plants, allowed to dry (four to six hours), and then the plants were inoculated with the fungus. Each test utilized control plants which were sprayed with the water, acetone, and methanol mixture and inoculated with the fungus. The remainder of the technique of each of the tests is given below and the results are reported as percent disease control (percentages of plants treated with the compounds of the present invention lacking disease signs or symptoms compared to the untreated control plants).

Cucumber Downy Mildew (CDM)

*Pseudoperonospora cubensis* was maintained on leaves of live Marketer cucumber plants in a constant temperature room at 65° F. to 75° F. in humid air with moderate light intensity for 7 to 8 days. A water suspension of the spores from infested leaves was obtained and the spore concentration was adjusted to about 100,000 per ml of water.

Marketer cucumber seedlings were inoculated by spraying the underside of the leaves with a DeVilbiss atomizer until small droplets were observed on the leaves. The inoculated plants were incubated in a mist chamber for 24 hours at about 70° F. and then subsequently incubated for 6 to 7 days in a controlled temperature room under mist at 65° F. to 75° F. Seven days after inoculation, the percent disease control was determined.

Rice Blast (RB)

*Piricularia oryzae* (about 20,000 conidia per ml) was used to innoculate Nato rice plants by spraying the leaves and stems with an airbrush until a uniform film of inoculum was observed on the leaves. The inoculated plants were incubated in a humid environment (75° F. to 85° F.) for about 24 hours, then placed in a greenhouse environment (70° F. to 75° F.). Seven to eight days after inoculation, the percent disease control was determined.

Rice Sheath Blight (RSB)

*Pellicularia filamentosa* (f. sp. sasiki) was cultured on an autoclaved mixture of crushed rice seeds and potato dextrose broth (100 g of rice seeds per 30 ml of potato dextrose broth) in a 500 ml Erlenmeyer flask. After 10 days, the culture was blended in a blender to produce a uniform inoculum. Approximately one teaspoon of inoculum was spread among Lebonnet rice seedlings on the soil surface of each pot (3 inch diameter). The inoculated seedlings were incubated for 5 days in a humidity cabinet (85° F. to 90° F.). Percent disease controls were determined immediately after removing the seedlings from the cabinet.

Tomato Late Blight (TLB)

*Phytophthora infestans* was cultured on four week old Pixie tomato plants in a controlled environment room (65° F. to 70° F. and 100% relative humidity). After storage, the spores were washed from the leaves with water and dispersed by DeVilbiss atomizer over three week old Pixie tomato plants which had been sprayed previously with experimental fungicides. The inoculated plants were placed in a humidity cabinet at 70° F. and constant mist for 24 hours for infection. The plants were then moved to the controlled environment room as above and scored after three more days incubation. Disease control levels were recorded as percent control four days after inoculation and five days after spraying the compounds.

Wheat Powdery Mildew (WPM)

*Erysiphe graminis* (f. sp. tritici) was cultured on Pennol wheat seedlings in a controlled temperature room at 65° F. to 75° F. Mildew spores were shaken from the culture plants onto Pennol wheat seedlings which had been sprayed previously with the fungicide compound. The inoculated seedlings were kept in a controlled temperature room at 65° F. to 75° F. and subirrigated. The percent disease control was rated 8 to 10 days after the inoculation.

Wheat Leaf Rust (WLR)

*Puccinia recondita* (f. sp. tritici Races PKB and PLD) was cultured on seven day old wheat (cultivar Fielder) over a 14 day period in the greenhouse. Spores were collected from the leaves with a cyclone vacuum or by settling on aluminum foil. The spores were cleaned by sieving through a 250 micron opening screen and stored or used fresh. Storage employed sealed bags in an Ultralow freezer. When stored, spores must be heat shocked for two minutes at 40° F before use. A spore suspension is prepared from dry uredia by adding 20 mg (9.5 million) per ml of Soltrol oil. The suspension is dispensed into gelatin capsules (0.7 ml capacity) which attach to the oil atomizers. One capsule is used per flat of twenty of the two inch square pots of seven day old Fielder wheat. After waiting for at least 15 minutes for the oil to evaporate from the wheat leaves, the plants are placed in a dark mist chamber (18°–20° C and 100% relative humidity) for 24 hours. The plants are then put in the greenhouse for the latent period and scored after 10 days for disease levels. Protective and curative tests were inoculated one day after and two days, respectively, before spraying the plants with the test chemicals.

Wheat Leaf Blotch (SNW)

*Septoria nodorum* was maintained on Czapek-Dox V-8 Juice agar plates in an incubator in the dark at 20° C. for 48°–72 hours, then incubated at 20° C. with alternating light and dark (12 hours:12 hours). A water suspension of the spores, obtained from the plates by shaking the portion of the plate with fungal material in deionized water and filtering through cheesecloth, was diluted to a spore concentration of $3.0 \times 10^6$ per milliliter. The innoculum was dispersed by a DeVilbiss atomizer over one week old Fielder wheat plants which had been sprayed previously with the fungicide compound. The innoculated plants were placed in a humidity cabinet at 20° C. with 12 hour:12 hour light/dark cycles for 96 hours. The innoculated seedlings were then moved to a controlled environment room as above and scored after 8 more days incubation. Disease control levels were recorded as percent control ten days after innoculation.

TABLE 4

Greenhouse Test Results of Plant Diseases Control

| Compound | Rate (ppm) | % Control | | | | |
|---|---|---|---|---|---|---|
| | | CDM | RB | TLB | WLR | WPM |
| 1 | 200 | 90 | — | 0 | 80 | 0 |
| 2 | 200 | 0 | — | 0 | 85 | 75 |
| 3 | 200 | 50 | — | 0 | 0 | 40 |

TABLE 4-continued

Greenhouse Test Results of Plant Diseases Control

| Compound | Rate (ppm) | CDM | RB | TLB | WLR | WPM |
|---|---|---|---|---|---|---|
| 4 | 200 | 50 | — | 95 | 0 | 25 |
| 5 | 200 | 40 | — | 95 | 0 | 0 |
| 7 | 200 | 50 | — | 90 | 0 | 0 |
| 11 | 100 | 100 | 95 | 0 | 50 | 85 |
| 12 | 200 | 0 | 95 | 0 | 25 | 0 |
| 13 | 200 | 80 | — | 70 | 90 | 0 |

These compounds were further evaluated in a secondary greenhouse test for their dose response against the following diseases: rice blast, rice sheath blight, tomato light blight, wheat leaf rust, and wheat powdery mildew. These results are shown in Table 5.

TABLE 5

Secondary Greenhouse Test Results of Plant Diseases Control

| Compound | Rate (ppm) | RB | RSB | TLB | WLR | WPM |
|---|---|---|---|---|---|---|
| 1 | 200 | 50 | 75 | 95 | 80 | 50 |
|   | 50 | 50 | 50 | 75 | 50 | 0 |
| 2 | 200 | 75 | 0 | 75 | 90 | 50 |
|   | 50 | 50 | 0 | 50 | 80 | 50 |
| 3 | 200 | 50 | 0 | 95 | 95 | 50 |
|   | 50 | 50 | 0 | 0 | 0 | 50 |
| 4 | 200 | 50 | 50 | 0 | 0 | 50 |
|   | 50 | 50 | 50 | 0 | 0 | 0 |
| 5 | 200 | — | — | — | — | — |
|   | 50 | 50 | 25 | 0 | 0 | 50 |
| 7 | 200 | 50 | 50 | 90 | 80 | 50 |
|   | 50 | 50 | — | 50 | 50 | 0 |
| 8 | 200 | — | — | 50 | 90 | 50 |
|   | 50 | — | — | 50 | 80 | 0 |
|   | 200 | 50 | 75 | — | — | — |
|   | 50 | 50 | 50 | — | — | — |
| 13 | 200 | 50 | 75 | 50 | 90 | 75 |
|   | 50 | 50 | 50 | 0 | 50 | 50 |

These compounds, along with their corresponding non-iodopropargylated derivatives, were further evaluated in an advanced greenhouse test at a rate of 0.25 kg a.i./ha. These data, as percent disease control, are presented in Table 6. The compounds identified with a prime (') were the non-iodo analogues of the invention compounds, i.e., the compounds of formula III or IV.

TABLE 6

Advanced Greenhouse Comparative Testing

| Compound | TLB | CDM | WLR | SNW | WPM | Average |
|---|---|---|---|---|---|---|
| 1 | 50.0 | 100.0 | 90.0 | 65.0 | 65.0 | 74.0 |
| 2 | 38.0 | 98.0 | 83.0 | 90.0 | 53.0 | 72.4 |
| 3 | 52.0 | 100.0 | 75.0 | 47.0 | 65.0 | 67.8 |
| 4 | 30.0 | 100.0 | 80.0 | 53.0 | 63.0 | 65.2 |
| 5 | 28.0 | 100.0 | 80.0 | 72.0 | 67.0 | 69.4 |
| 6 | 70.0 | 100.0 | 82.0 | 68.0 | 68.0 | 77.6 |
| 1'* | — | — | — | — | — | — |
| 2' | 20.0 | 8.0 | 68.0 | 48.0 | 55.0 | 39.8 |
| 3' | 27.0 | 8.0 | 53.0 | 52.0 | 58.0 | 39.6 |
| 4' | 20.0 | 87.0 | 70.0 | 87.0 | 90.0 | 70.8 |
| 5' | 18.0 | 100.0 | 62.0 | 57.0 | 67.0 | 60.8 |
| 6' | 17.0 | 97.0 | 62.0 | 60.0 | 72.0 | 61.6 |

*Compound 1' was not tested.

Although the invention has been described in detail herein, various alternatives, improvements, and modifications should become apparent to those skilled in the art without departing from the spirit and scope of this invention.

What is claimed is:

1. N-iodopropargyl hydantoin compounds having a structure according to Formula I or Formula II:

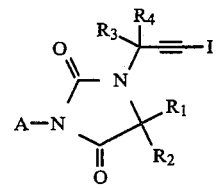

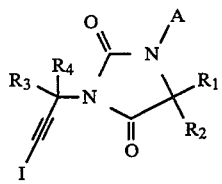

wherein A is selected from $C_1$ to $C_{12}$ straight or branched alkyl; benzyl; allyl; $C_3$-$C_6$ alkynyl optionally substituted with halogen; and hydrogen;

$R_1$, $R_2$ are independently selected from hydrogen; $C_1$-$C_3$ alkyl; and phenyl optionally substituted with halogen, nitro, alkoxy ($C_1$-$C_3$), or haloalkyl ($C_1$-$C_3$); or may be joined together along with the hydantoin ring carbon to which they are attached to form a saturated ($C_3$-$C_7$) or unsaturated ($C_5$-$C_7$) spiro ring; and $R_3$, $R_4$ are independently hydrogen or $C_1$-$C_3$ alkyl.

2. Compound according to claim 1 wherein A is selected from benzyl; n-butyl; n-octyl; 3-iodo-2-propynyl; and 1,1-dimethyl-3-iodo-2-propynyl.

3. Compound according to claim 2 wherein $R_1$ and $R_2$ together form a spirocyclohexane ring.

4. Compound according to claim 2 selected from the group consisting of 1-(3-iodo-2-propynyl)-3-benzyl-5,5-dimethylhydantoin;

1-(3-iodo-2-propynyl)-3-n-butyl-5,5-dimethylhydantoin;

1-(3-iodo-2-propynyl)-3-n-octyl-5,5-dimethylhydantoin;

1,3-bis-(3-iodo-2-propynyl)-5,5-dimethylhydantoin;

3-(3-iodo-2-propynyl)-5,5-dimethylhydantoin;

3-(3-iodo-2-propynyl)-1-benzyl-5,5-dimethylhydantoin; and 3-(3-iodo-2-propynyl)-hydantoin.

5. A method of controlling or inhibiting the growth of microbes comprising applying a microbialdally effective amount of a compound according to claim 1 at, into, or onto a locus which is subject to microbial attack.

6. An agricultural fungitidal composition which comprises an agriculturally acceptable carrier and a fungicidally effective amount of a compound according to claim 1.

* * * * *